(12) United States Patent
Landatxe Zugarramurdi et al.

(10) Patent No.: US 11,079,348 B2
(45) Date of Patent: Aug. 3, 2021

(54) WATER SENSOR FOR DETECTING WATER IN GAS OIL FILTERS

(71) Applicant: CEBI ELECTROMECHANICAL COMPONENTS SPAIN, S.A., Villatuerta (ES)

(72) Inventors: Jose Luis Landatxe Zugarramurdi, Villatuerta (ES); Sergio Diez Garcia, Villatuerta (ES); Javier Garcia Izaguirre, Villatuerta (ES); Jorge Machin Mindan, Villatuerta (ES); Enrique Breton Cristobal, Villatuerta (ES)

(73) Assignee: CEBI ELECTROMECHANICAL COMPONENTS SPAIN, S.A., Villatuerta (ES)

( * ) Notice: Subject to any disclaimer, the term of this patent is extended or adjusted under 35 U.S.C. 154(b) by 91 days.

(21) Appl. No.: 16/497,652

(22) PCT Filed: Mar. 27, 2018

(86) PCT No.: PCT/ES2018/070244
§ 371 (c)(1),
(2) Date: Sep. 25, 2019

(87) PCT Pub. No.: WO2018/178463
PCT Pub. Date: Oct. 4, 2018

(65) Prior Publication Data
US 2020/0271607 A1    Aug. 27, 2020

(30) Foreign Application Priority Data

Mar. 30, 2017   (ES) ............................... ES201700330

(51) Int. Cl.
*G01R 31/01*    (2020.01)
*G01N 27/22*    (2006.01)
(Continued)

(52) U.S. Cl.
CPC ........... *G01N 27/223* (2013.01); *B01D 17/12* (2013.01); *B01D 36/005* (2013.01); *G01N 27/228* (2013.01)

(58) Field of Classification Search
USPC ................................. 324/664, 689, 694, 594
See application file for complete search history.

(56) References Cited

U.S. PATENT DOCUMENTS

2009/0108914 A1* 4/2009 Zhang .................. H03K 17/962
                                                                    327/517
2009/0320587 A1    12/2009 Siemens et al.
(Continued)

FOREIGN PATENT DOCUMENTS

| ES | 2530691 A1 | 3/2015 |
|----|------------|--------|
| ES | 2597165 A1 | 1/2017 |
| WO | 2016016172 A1 | 2/2016 |

OTHER PUBLICATIONS

International Search Report for Corresponding International Application No. PCT/ES2018/070244 (2 Pages) (dated Aug. 21, 2018).

*Primary Examiner* — Vincent Q Nguyen
(74) *Attorney, Agent, or Firm* — Lucas & Mercanti, LLP

(57) ABSTRACT

A water sensor for detecting water in gas oil filters having a first and a second electrode a first and a second earth connection for earthing the first electrode and the second electrode; a first switch arranged in the first earth connection; a second switch arranged in the second earth connection; a first and a second current connection for injecting a first current into the first electrode and a second current into the second electrode; and a current-generating circuit connected to the first electrode and to the second electrode through the first current connection and the second current connection respectively, and designed to inject the first (Continued)

current into the first electrode and the second current into the second electrode, the first current and the second current being the same.

3 Claims, 1 Drawing Sheet

(51) Int. Cl.
*B01D 17/12* (2006.01)
*B01D 36/00* (2006.01)

(56) References Cited

U.S. PATENT DOCUMENTS

| | | |
|---|---|---|
| 2013/0031963 A1 | 2/2013 | Ritchie, Jr. et al. |
| 2016/0041021 A1 | 2/2016 | Saitou et al. |
| 2018/0031505 A1* | 2/2018 | Diez Garcia .......... G01N 27/07 |

* cited by examiner

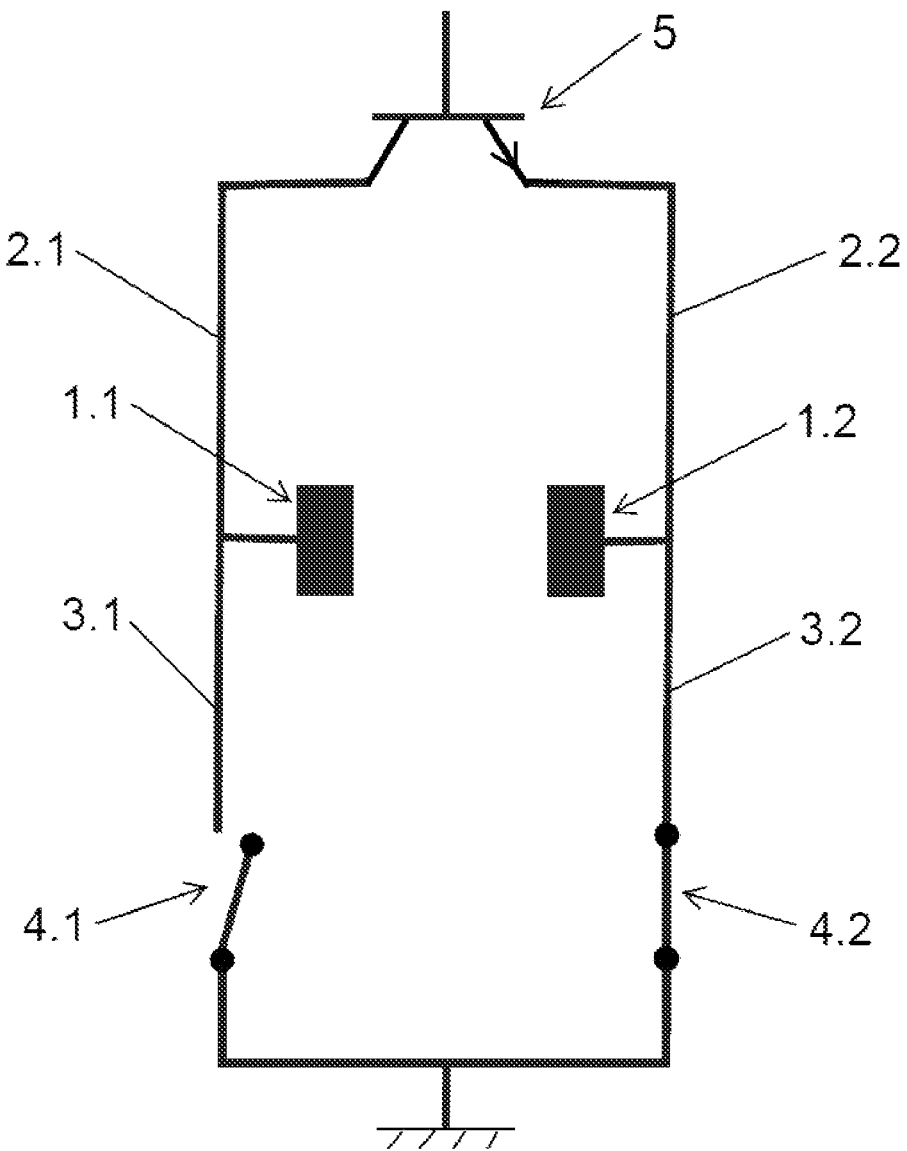

WATER SENSOR FOR DETECTING WATER IN GAS OIL FILTERS

CROSS REFERENCE TO RELATED APPLICATION

This Application is a 371 of PCT/ES2018/070244 filed on Mar. 27, 2018, which, in turn, claimed the priority of Spanish Patent Application No. P201700330 filed on Mar. 30, 2017, both applications are incorporated herein by reference.

TECHNICAL FIELD

The present invention relates to the industry dedicated to diesel engine fuel filters, and more specifically to the industry dedicated to detecting water in diesel engine fuel filters, proposing a water sensor for carrying out this detection.

STATE OF THE ART

Currently, the need exists for a way to remove water from diesel engine fuel contained therein to prevent said water from coming into contact with sensitive elements in the injection systems of said engines, on which water can have a damaging effect due to corrosion phenomena, such as oxidation and deposition of insoluble salts.

By using gas oil filters, water is separated from the gas oil. The water that is separated from the fuel of the diesel engines settles and collected in a region defined for that purpose which, given that water is denser than gas oil, is usually located in the lower portion of the gas oil filter enclosure.

Water sensors are arranged in gas oil filters. By means of these sensors, when the settled water reaches a pre-determined maximum level in the lower portion of the gas oil filter enclosure, a warning signal is emitted. The warning signal indicates the need to remove the collected water before it damages the engine. To detect the water, these sensors include two metal electrodes arranged in correspondence with the mentioned lower portion of the enclosure.

The accumulation of water separated from the gas oil in gas oil filters in the water settling region is known to be detected using complex water sensors, while the effectiveness in said detection is prolonged over time by injecting electric current into the electrodes non-continuously or intermittently.

It is known through document ES2530691B1 to alternate the injection of electric current into one electrode then the other, meaning alternating the anode and cathode function between the two electrodes, so as to compensate for and reduce the corrosion phenomena generated in each of the electrodes as a consequence of current circulating through same. To do so, a switching bridge including an H-shaped structure with four switches that can be actuated two-by-two by means of control signals is known to be used.

This solution, however, entails a large number of electronic components, which results in a complex operation, in addition to difficulties in miniaturising water sensors for their placement in increasingly smaller spaces. Likewise, the cost of water sensors is high as a consequence of the large number of said switches or breakers.

Therefore, a water sensor for detecting the presence of water in gas oil filters is necessary which is effective against corrosion phenomena, and also entails a reduction in the cost and volume thereof.

OBJECT OF THE INVENTION

For the purpose of fulfilling this objective and solving the technical problems discussed up to this point, in addition to providing additional advantages that can be seen below, the present invention relates to a water sensor for detecting the presence of water in gas oil filters, which in addition to being effective, results in a reduction in the total volume as well as of the final cost thereof.

The water sensor for detecting water in gas oil filters comprises a first electrode and a second electrode; a first earth connection for earthing the first electrode; a second earth connection for earthing the second electrode; a first switch arranged in the first earth connection; and a second switch arranged in the second earth connection.

The water sensor object of the invention additionally comprises a first current connection for injecting a first current into the first electrode; a second current connection for injecting a second current into the second electrode; and a current-generating circuit connected to the first electrode and to the second electrode by means of the first current connection and the second current connection, respectively.

The current-generating circuit is designed to inject the first current into the first electrode and the second current into the second electrode, the first current and the second current being the same.

The water sensor is thereby provided such that it can detect the presence of water in fuel filters, the useful life thereof being prolonged and the electronic components used being reduced in volume and cost. Therefore, with the total volume being reduced, the water sensor provides advantages also from the viewpoint of the location thereof, as it requires a smaller space and offers greater flexibility for the location of other electronic and/or mechanical elements around it.

The current-generating circuit is a current mirror. The water sensor is thereby provided with a simplified design in reference to the power supply or injection of the first and the second electric currents.

The water sensor for detecting water in gas oil filters additionally comprises a controller designed for acting alternately on the first switch and the second switch such that the earth connection of the first electrode and the second electrode is alternated. The operations of the water sensor are therefore simplified, which brings greater reliability and a longer useful life.

DESCRIPTION OF THE FIGURES

FIG. 1 schematically shows a switching bridge which is comprised in a water sensor object of the present invention.

DETAILED DESCRIPTION OF THE INVENTION

The invention relates to a sensor of for detecting water in gas oil filters. The water sensor comprises two electrodes (1.1, 1.2), a first electrode (1.1) and a second electrode (1.2). Additionally, the water sensor comprises a first current connection (2.1) for injecting a first current into the first electrode (1.1), a second current connection (2.2) for injecting a second current into the second electrode (1.2), a first earth connection (3.1) for earthing the first electrode (1.1), a second earth connection (3.2) for earthing the second electrode (1.2), a first switch (4.1) arranged in the first earth connection (3.1) and a second switch (4.2) arranged in the second earth connection (3.2).

Additionally, the water sensor comprises a current-generating circuit (5) connected to the first electrode (1.1) and to the second electrode (1.2) by means of the first current connection (2.1) and the second current connection (2.2), respectively. The current-generating circuit (5) is designed such that it injects the first current into the first electrode (1.1) and the second current into the second electrode (1.2), the first current and the second current being the same.

According to this, the current circuit is a current mirror. Thus, the first current and the second current have the same nominal value. Preferably, the first current and the second current are direct currents.

The water sensor is devoid of switches in the first current connection (2.1) and in the second current connection (2.2). Meaning, by means of the first current connection (2.1) and the second current connection (2.2), the first electrode (1.1) and the second electrode (1.2), respectively, are directly connected to the current-generating circuit (5).

The water sensor is designed to alternate the earth connection between the first electrode (1.1) and the second electrode (1.2). To do so, the water sensor comprises a controller, not shown in FIG. 1, designed to open and close the first switch (4.1) and the second switch (4.2) in an alternating manner. When the first switch (4.1) is closed, that is, the first electrode (1.1) is earthed, the second switch (4.2) is open, that is, the second electrode (1.2) is not earthed. Thus, when the first switch (4.1) is open, the second switch (4.2) is closed.

The two electrodes (1.1, 1.2) are permanently connected to the current-generating circuit (5) and the current-generating circuit (5) is permanently injecting the first current and the second current; however, each of the two electrodes (1.1, 1.2) receives the current injection in a discontinuous or alternating manner. With a measurement cycle being established as an opening and a closing of each of the two switches (4.1, 4.2), in any measurement semi-cycle or half-cycle, electric current of the two electrodes (1.1, 1.2) is only injected into the one with the corresponding switch (4.1, 4.2) thereof open.

According to this, in a first phase, electric current is injected into a medium wherein the two electrodes (1.1, 1.2) are arranged from the current-generating circuit (5) through the first electrode (1.1) as the first switch (4.1) is open, whereas the second electrode (1.2) is earthed or grounded as the second switch (4.2) is closed. In a second phase, electric current is injected into the medium through the second electrode (1.2) as the second switch (4.2) is open, whereas the first electrode (1.1) is earthed or grounded as the first switch (4.1) is closed. The anode and cathode function of the two electrodes (1.1, 1.2) are thereby alternated in each of the phases which are successively repeated. This alternation prolongs the useful life of the water sensor.

With the water sensor installed in the gas oil filter and the two electrodes (1.1, 1.2) immersed in the medium stored in a water settling region of said filter, the two electrodes (1.1, 1.2) and the medium form a system. This method involves shorting to earth or ground the current-generating circuit (5). Said shorting is assumed when the nominal value of the first current and the second current is a low value such that it does not produce any noticeable power dissipation through the switch (4.1, 4.2) through which it is bypassed to earth or ground, or any noticeable increase in the voltage in said switch (4.1, 4.2), which may interfere with the voltage of the mentioned system and with the evaluation of the discrimination or measurement voltage which determines the presence of water.

The fact that electric current is flowing at all times can likewise be advantageous from the viewpoint of eliminating unwanted switching transients, as well as reducing the electrical disturbances given off into the environment.

The invention claimed is:

1. A water sensor for detecting water in gas oil filters, comprising:
   a first electrode and a second electrode;
   a first earth connection for earthing the first electrode;
   a second earth connection for earthing the second electrode;
   a first switch arranged in the first earth connection;
   a second switch arranged in the second earth connection;
   a first current connection for injecting a first current into the first electrode;
   a second current connection for injecting a second current into the second electrode; and
   a current-generating circuit connected to the first electrode and to the second electrode through the first current connection and the second current connection respectively;
   wherein the current-generating circuit is designed to inject the first current into the first electrode and the second current into the second electrode, the first current and the second current being the same.

2. The water sensor according to claim 1, wherein the current-generating circuit is a current mirror.

3. The water sensor according to claim 1, further comprising a controller designed to act alternately on the first switch and the second switch such that the earth connection of the first electrode and the second electrode is alternated.

\* \* \* \* \*